United States Patent [19]

Meng et al.

[11] Patent Number: 5,654,431

[45] Date of Patent: Aug. 5, 1997

[54] 5-ALKOXY TRYPTAMINE DERIVATIVES

[76] Inventors: Qingchang Meng, 19 McKinnon Avenue, Georgetown, Ontario, Canada, L7G 5H5; Abdelmalik Slassi, 440 McMurchy Avenue, Apt. 1017, Brampton, Ontario, Canada, L6Y 2N5; Sumanas Rakhit, 1110 Queen St W., #26, Mississauga, Ontario, Canada, L5H 4J4

[21] Appl. No.: 655,588

[22] Filed: May 30, 1996

[51] Int. Cl.$^6$ .................. C07D 209/08; C07D 221/06
[52] U.S. Cl. .................. 546/98; 548/208; 548/210; 548/451; 548/455; 548/468; 548/503
[58] Field of Search .................. 548/455, 210, 548/208, 451, 503, 468; 546/98

[56] References Cited

FOREIGN PATENT DOCUMENTS 9520588  8/1995  WIPO.
9530655  11/1995  WIPO.

OTHER PUBLICATIONS

CA114:178477w 5–HT$_{1D}$ serotonin . . . investigation. Glennon et al., p. 84, 1991.
CA122:2652446 b Preparation . . . ligands. Halazy et al., p. 1091, 1995.
CA 121:179613u Preparation of . . . ligands, Halazy et al. p. 1085, 1994.

*Primary Examiner*—Joseph K. McKane
*Attorney, Agent, or Firm*—Ridout & Maybee

[57] ABSTRACT

Novel 5-alkoxy tryptamine derivatives are provided, corresponding to the general formula:

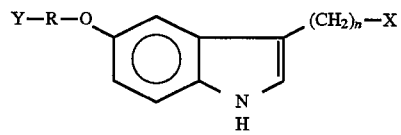

in which R may be alkaline, X may be amino, and Y is various N-heterocyclic or N-branched chain moieties. The compounds show selective binding to 5-HT$_{1D}$ receptor subtypes, and have potential pharmaceutical utility in manufacture of migraine-treating drugs.

56 Claims, No Drawings

5-ALKOXY TRYPTAMINE DERIVATIVES

FIELD OF THE INVENTION

This invention relates to novel chemical compounds active on the central nervous system (CNS). More particularly, it relates to novel tryptamine derivatives exhibiting selectivity towards certain human cell receptors, commonly known as serotonin or 5-HT receptors, and to compositions and uses of these novel compounds.

BACKGROUND OF THE INVENTION

Receptors are proteins disposed on the surface of cells. Serotonin, or 5-hydroxytryptamine, receptors are stimulated by serotonin (5-HT) and have been extensively studied. At least seven such 5-HT receptor types are known, denominated $5\text{-}HT_1$, $5\text{-}HT_2$, ... $5\text{-}HT_7$. 5-HT binds to different ones of these receptors in different ways, to give a signature profile.

The 5-HT receptor types can be further subdivided into subtypes; for example, receptor $5\text{-}HT_1$ has at least five subtypes denoted A, B, C, D and E. Within an individual subtype there may be further subdivisions. Thus $5\text{-}HT_{1D}$ subdivides to $5\text{-}HT_{1D\alpha}$ and $5\text{-}HT_{1D\beta}$.

It is desirable to find pharmaceutical compounds having a high degree of selectivity to a single receptor so that the drug thereof will exhibit reduced side effects.

Given the physiological and clinical significance of the $5\text{-}HT_{1D}$ receptor, it would be desirable to provide compounds capable of binding tightly and selectively to this receptor. Such compounds have potential medical use, for example, to treat migraine and other disorders for which administration of $5\text{-}HT_{1D}$ ligand is indicated.

DESCRIPTION OF THE PRIOR ART

Sumatriptan, or 3-[2-(dimethylamino)ethyl]-N-methyl-1H-indole-5-methanesulfonamide, of formula:

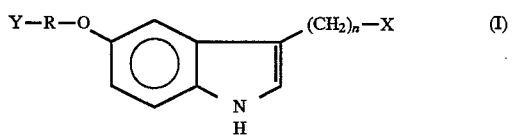

is an example of a pharmaceutical compound, currently on the market, which is a 5-HT receptor binder. It is prescribed for the treatment of migraine. It binds selectively to the receptor $5\text{-}HT_{1F}$ and to the receptor $5\text{-}HT_{1D}$, with high affinity and to the substantial exclusion of other 5-HT receptors.

International Patent Publication WO 95/30655 Glennon discloses tryptamine analogs having an aminoethyl or (N-alkyl)aminoethyl substituent at position 3 of the indole nucleus and various arylalkyl, arylalkanoyl and arylalkanoyloxy groups at position 5 thereof. These are disclosed to be selective for binding to $5\text{-}HT_{1D}$.

International patent publication WO 95/20588 The Wellcome Foundation Limited (PCT/GB95/00142) discloses tryptamine analogs substituted at position 3 of the indole nucleus with cycloalkyl-amino groups, and substituted at position 5 of the indole nucleus with, inter alia, alkylene-N-heterocyclic groups such as alkylene-phthalimido. They are presented as compounds which are selective agonists at the $5\text{-}HT_1$ subtype of the 5-HT receptor. Example 7 discloses 2-{2-[3-(trans-3-dimethylaminocyclobutyl)-1H-indol-5-yl]ethyl}phthalimide.

SUMMARY OF THE INVENTION

It is an object of the present invention to provide novel 5-substituted tryptamine derivatives.

It is a further object of the invention to provide such compounds which exhibit a high degree of binding selectivity towards the $5\text{-}HT_{1D}$ receptor subtype.

According to the present invention, there are provided novel 5-alkoxy-tryptamine derivatives exhibiting selectivity towards $5\text{-}HT_{1D}$ receptors, and corresponding to general formula I:

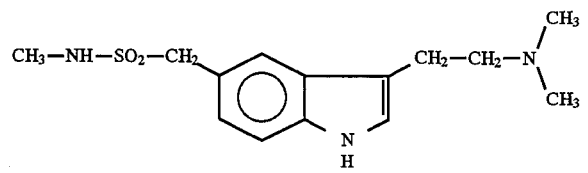

wherein:

n is an integer from 1–3;

R represents a straight or branched alkylene chain of from 1 to 9 carbon atoms optionally interrupted by a phenylene group;

X represents amino, mono(loweralkyl)amino, di(loweralkyl)amino or optionally N-lower alkyl-substituted pyrrolidine;

and Y represents optionally substituted phthalimide, benzosulfonimide, naphthosultam, naphthalimide, isoindolone, camphorsultam, toluenesulfonamido, N,N'-dicarboxylated guanidino or N-carboxylated amino, each of which is linked to R via a respective N-group thereof.

Compounds of the present invention exhibit selective binding for the $5\text{-}HT_{1D}$ receptor, indicative of potential utility in treatment of indications such as migraine and others for which administration of a $5\text{-}HT_{1D}$ ligand is indicated, and also for research and diagnostic use, for example to identify these receptors and to screen for drug candidates.

DESCRIPTION OF THE PREFERRED EMBODIMENTS

Preferred among the 5-alkoxy-tryptamine derivatives of the present invention are those of the general formula I given above in which integer n is 1 or 2, for example 3-ethylamine compounds and 1-methyl-pyrrolidine compounds. When group X is chosen to be pyrrolidine, it can be attached to the alkylene radical either through its hetero-N-group or through a carbocylic group, thereby leaving the N-group thereof available for substitution with lower alkyl. The term "lower alkyl" as used herein means alkyl groups of 1–4 carbon atoms.

In the preferred compounds according to the invention, R is a straight or branched alkylene group of from 2 to 6 carbon atoms, optionally interrupted by a phenylene group.

The compounds of the present invention have stereoisomeric forms, e.g. in respect of the configuration of the group at the 3-position of the indole nucleus. The present invention extends to cover the various isomers of compounds according to formula I above, as well as mixtures thereof. Pharmaceutically acceptable forms of the compounds, such as addition salts and hydrates, are also encompassed by the invention.

A first class of preferred compounds according to the present invention is those in which group Y is optionally substituted phthalimido, i.e. of formula:

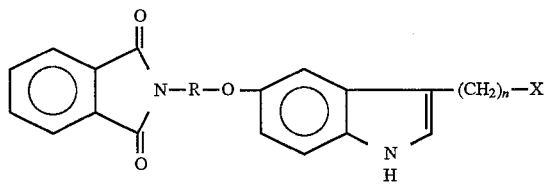

with the benzene ring thereof having from 0–4 halogen substituents, such as chloro. The alkylene chain R is preferably uninterrupted and comprises 3–5, most preferably 4, methylene groups.

A second class of preferred compounds according to the invention is those in which group Y is benzosulfonimido, i.e. of formula

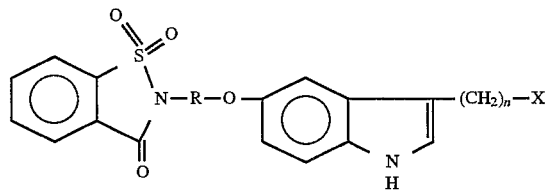

Again, the alkylene chain R is preferably uninterrupted, and comprises 3–5, preferably 4, methylene groups.

A third class of preferred compounds according to the invention is those in which group Y is naphthosultam, i.e. of formula:

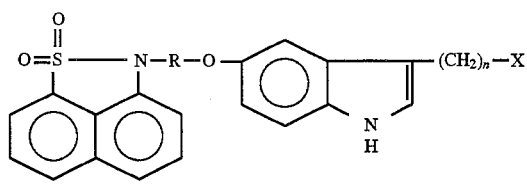

The alkylene chain R is preferably either uninterrupted, or interrupted by a 1,2- or 1,3-phenylene group, and comprises 3–5, preferably 4, methylene groups.

A fourth class of preferred compounds according to the invention is those in which group Y is naphthalimido, of formula:

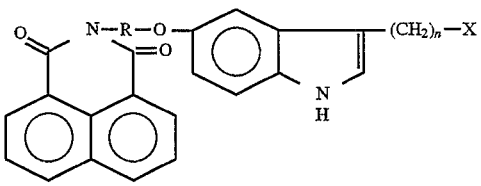

or of formula:

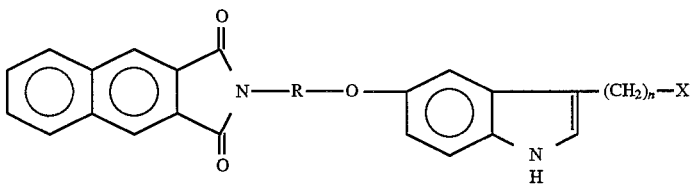

The alkylene chain R in either case is preferably uninterrupted, and comprises 3–5, preferably 4, methylene groups.

A fifth class of preferred compounds according to the invention is those in which group Y is isoindolone, i.e. of formula:

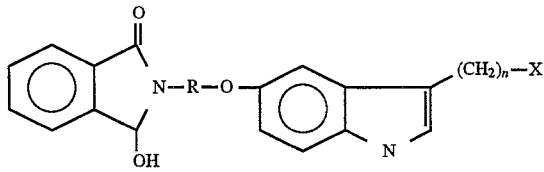

The alkylene chain R is preferably uninterrupted, and comprises 3–5, preferably 4, methylene groups.

A sixth class of preferred compounds according to the invention is those in which group Y is camphorsultam, i.e. of formula:

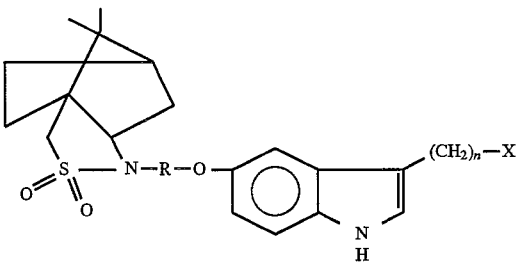

The alkylene chain R is preferably uninterrupted, and comprises 3–5, preferably 4, methylene groups.

A seventh class of preferred compounds according to the invention is those in which group Y is toluenesulfonamido, e.g. of formula:

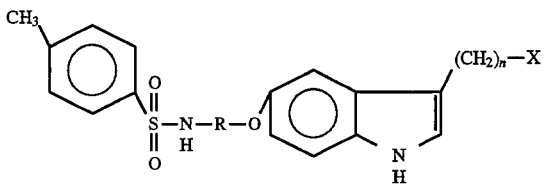

and analogues thereof in which the methyl group of the toluene ring is ortho- or meta-disposed relative to the sulfonamido group. The alkylene chain R is preferably uninterrupted, and comprises 3–5, preferably 4, methylene groups.

An eighth class of preferred compounds according to the invention is those in which Y is N,N'-dicarboxylated guanidino, e.g. of formula

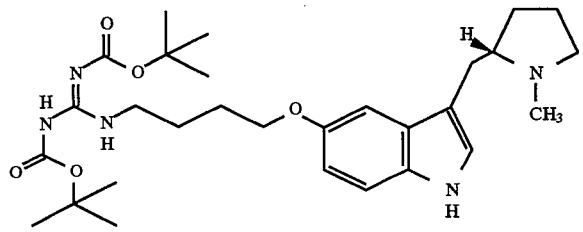

i.e. 3-(N-methylpyrrolidin-2S-ylmethyl)-5-(4-(bis-t-butyloxycarbonylguanidino)butyloxy)-1H-indole.

A ninth class of preferred compounds according to the present invention is those in which group Y is carboxylated amino such as N-carbobenzyloxy and N-(t-butyloxycarbonyl), e.g. of formula:

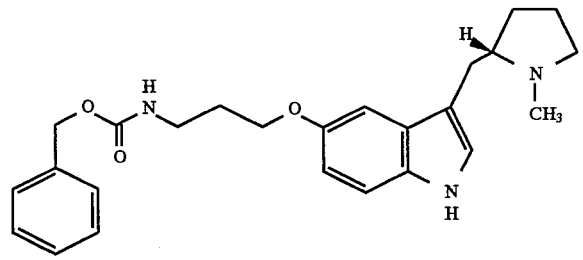

and of formula:

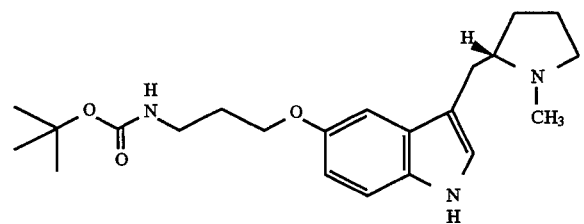

In all of the above classes of compound, uninterrupted, straight alkylene chains of 4 carbon atoms are preferred for group R. Such compounds appear to offer the largest degree of specificity as between 5-$HT_{1D\alpha}$ and 5-$HT_{1A}$ subtypes of serotonin receptors.

Specific, most preferred compounds according to this invention, on account of their selectivity towards the 5-$HT_{1D}$ receptors, are the following:

3-(N-methylpyrrolidin-2S-yl)methyl-5-(4-phthalimidobutyloxy)-1H-indole;

3-(2-aminoethyl)-5-[4-(1,8-naphthosultam-N-yl)butyloxy]-1H-indol; and 3-(2-aminoethyl)-5-(4-phthalmidobutyloxy)-1H-indole.

Compounds of the present invention can be synthesized by processes generally known in the field of organic chemical synthesis. Thus, in general terms, an indole compound substituted at position 3 with the desired grouping ($CH_2$)$_n$—X, or an immediate precursor thereof, and substituted in the 5 position by hydroxy, is first prepared, and then coupled with an alkylating agent Y—R—Z where Z is a suitable leaving group such as halogen (preferably chlorine, bromine or iodine) in the presence of a base in an inert solvent. Optionally the reaction solution also includes sodium or potassium iodide. Suitable bases include sodium or potassium carbonate or triethylamine. Suitable solvents include acetonitrile, acetone and N,N-dimethylformamide and the reaction can be performed at temperatures ranging from 0°–150° C. The preferred conditions are potassium carbonate in acetonitrile at temperatures from 25°–100° C.

Compounds Y—R—Z are either commercially available or can be prepared by procedures described in the art. For example, the corresponding phthalimide or substituted phthalimide, naphthalimide, naphthosultam, benzosulfonimide, camphorsultam or toluenesulfonamide (which are commercially available) can be reacted with bromo alcohol of the general formula HO—R—Br in the presence of triphenylphosphine and diethylazodicarboxylate in dichloromethane (see, for example, Mitsunobu, O. "Synthesis", 1981 1–28).

When Y is phthalimide or substituted phthalimide and Z is bromine, the compound Y—R—Z can, in the alternative, be obtained by reacting the corresponding anhydride (commercially available) with an amino alcohol of the general formula $H_2N$—R—OH in an inert solvent such as toluene under refluxing conditions followed by treatment of the resulting alcohol with triphenylphosphine and bromine in dichloromethane.

In the alternative, the 5-hydroxy group on the indole compound can first be elaborated e.g. by reaction with an appropriate dibromo compound, so as to create at position-5 an oxyalkylene group or an oxyalkylene group interrupted by a phenyl group and having a residual bromine group in a chain-terminal position. The residual bromine group can then be reacted with, for example, naphthalimide, to create an N-linkage to the naphthalimido or the like group, and thereby prepare compounds according to the preferred embodiments of the invention. This synthesis is particularly suitable for compounds having a phenyl-interrupted oxyalkylene group at position 5, since appropriate intermediates are readily prepared by reacting dibromoxylenes with the 5-hydroxy indole compounds.

The 3-substituted indole precursor compounds for coupling with Y—R—Z can be prepared by different methods known in organic chemical synthesis, depending on the choice of the 3-substituent, i.e. the grouping ($CH_2$)$_n$—X for the compounds of the present invention.

For the preparation of compounds according to the invention where n=1 and X represents 1-substituted-2-pyrrolidinyl, the precursor compound for reaction with Y—R—Z defined above is, for example, of formula III and can be prepared according to the following reaction scheme.

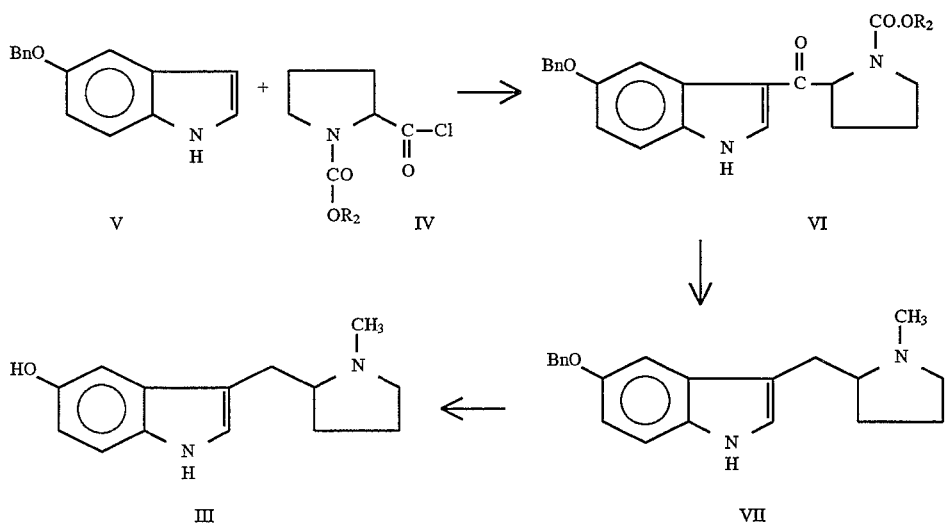

Compound IV in which $R_2$ is for example benzyl or t-butyl, can be condensed with the substituted indole compound V, typically by first converting the 5-benzyloxyindole V to a magnesium derivative by reaction with a suitable Grignard reagent, such as t-butyl or ethylmagnesium bromide, in an inert solvent. Then the magnesium derivative so formed can be reacted in situ with the reagent of formula IV to provide compounds of formula VI. Suitable inert solvents include tetrahydrofuran and diethylether (which is preferred). The reaction can be conducted at temperatures ranging from −30° to 65° C., suitably at room temperature. Compound VII is prepared from compound VI by reduction using a reducing agent such as lithium aluminum hydride in solution in an inert solvent such as dioxane, diethyl ether, similar other ethers or, preferably, tetrahydrofuran. Compound VII is converted to the free hydroxy compound by standard debenzylation procedures, for example catalytic hydrogenation (hydrogen gas in the presence of palladium on carbon as the catalyst in an inert solvent such as methanol or ethyl acetate or, preferably, a mixture of the two), to provide a compound of formula III. The free 2-carboxylic acid version of compound IV is known. The acyl chloride thereof is prepared by reaction of the free acid with oxalyl chloride and a trace amount of N,N-dimethylformamide in dichloromethane at temperatures ranging from −10° to 25° C.

For the preparation of compounds according to the present invention where n=2 and X is amino the precursor compound for reaction with Y—R—Z as defined above is a compound of formula VIII (wherein PG=protecting group) and can be prepared by methods known to one skilled in the art from a compound of formula IX, thus:

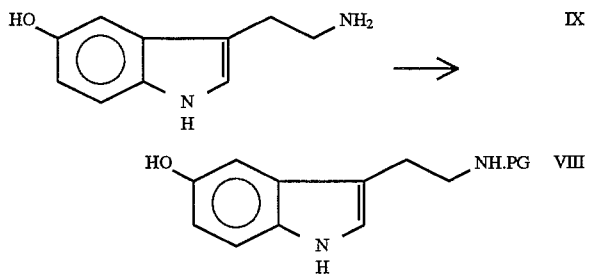

For example, this can be conducted using di-t-butyldicarbonate (BOC$_2$O), in the presence of potassium carbonate in water to introduce the t-butyloxycarbonyl protecting group. After the coupling of VIII with Y—R—Z as described above, the protecting group can be removed by standard deprotection procedures, for example, treating the 5-substituted-N-t-butylcarbonyloxy-1H-indole with HCl in ethyl acetate to provide compounds of formula I where X is amino. The compound of formula IX is commercially available, as its creatine sulfate monohydrate salt.

For the preparation of compounds according to he present invention where n=2 and X is mono(loweralkyl)amino or di(loweralkyl)amino or 1-pyrrolidinyl the precursor compound for reaction with Y—R—Z as defined above is a compound of formula X1, wherein $R_3$ and $R_4$ are H, lower alkyl or alkylene joined to to N to form the pyrrolidine ring, and can be prepared by methods known to one skilled in the art. Thus, a compound of formula V is reacted with oxalyl chloride followed by addition of the appropriate amine XII to provide a compound of formula XIII. This reaction is conducted in an inert solvent such as diethyl ether (preferred) or dichloromethane at temperatures in the range of 0°–65° C. Compounds of formula XIV are obtained by reduction of compounds of formula XIII using as a reducing agent, lithium borohydride, diborane or, preferably, lithium aluminum hydride in an inert solvent (dioxane, diethyl ether of tetrahydrofuran, which is preferred) at temperatures ranging from 25°–100° C., preferably at about 65° C. Compounds of formula XI are then obtained from compounds of formula XIV by standard debenzylation procedures, for example catalytic hydrogenation, as described above. The reaction may be represented thus:

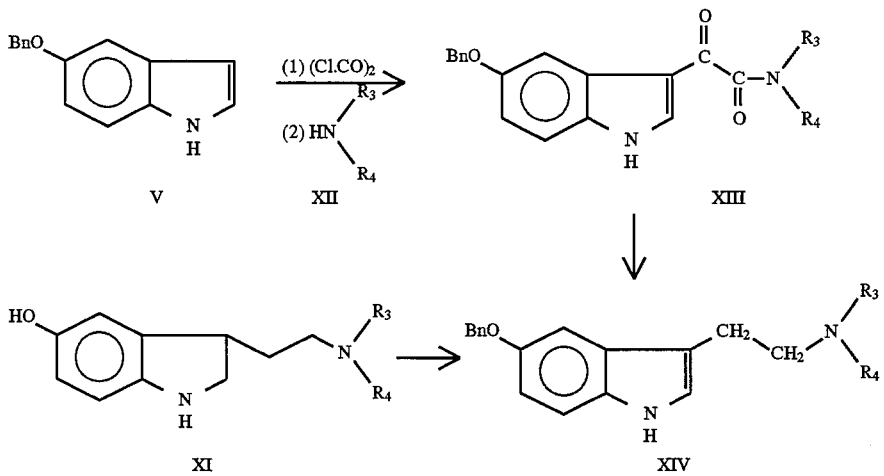

In an embodiment of the invention, the compound is provided in labelled form, such as radiolabelled form e.g. labelled by incorporation within its structure $^3$H or $^{14}$C or by conjugation to $^{125}$I. In another aspect of the invention, the compounds in labelled form can be used to identify 5-HT$_{1D\alpha}$ receptor ligands by techniques common in the art. This can be achieved by incubating the receptor in the presence of a ligand candidate and then incubating the resulting preparation with an equimolar amount of radiolabelled compound of the invention. 5-HT$_{1D\alpha}$ ligands are thus revealed as those that are not significantly displaced by the radiolabelled compound of the present invention. Alternatively, 5-HT$_{1D\alpha}$ ligand candidates may be identified by first incubating a radiolabelled form of a compound of the invention then incubating the resulting preparation in the presence of the candidate ligand. A more potent 5-HT$_{1D\alpha}$ ligand will, at equimolar concentration, displace the radiolabelled compound of the invention.

The serotonin-like binding affinity of the compounds indicates their utility as pharmaceuticals useful for the treatment of various conditions in which the use of a 5-HT$_{1D}$ ligand is indicated, such as for the treatment of migraine, cluster headache and portal tension, a condition characterized by increased portal vein blood flow and typically associated with cirrhosis of the liver.

For use in medicine, the compounds of the present invention are administered as standard pharmaceutical compositions. The present invention therefore provides in a further aspect pharmaceutical compositions comprising a compound of formula (I) or a pharmaceutically acceptable salt, solvate or hydrate thereof and a pharmaceutically acceptable carrier. Compounds of the present invention may be administered by any convenient route, for example by oral, parenteral, buccal, sublingual, nasal, rectal or transdermal administration and the pharmaceutical compositions adapted accordingly.

The compounds and their pharmaceutically acceptable salts which are active when given orally can be formulated as liquids, for example syrups, suspensions or emulsions; tablets, capsules and lozenges. Liquid formulations will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. Compositions in the form of tablets can be prepared using any suitable pharmaceutical carrier routinely used for preparing solid formulations. Examples include magnesium stearate, starch, lactose, sucrose and cellulose. Compositions in the form of capsules can be prepared using routine encapsulation procedures. For example, pellets containing active ingredient can be prepared using standard carriers and then filled into hard gelatin capsules; alternatively, a dispersion or suspension can be prepared using a suitable pharmaceutical carrier, for example aqueous gums, celluloses, silicates or oils and the dispersion or suspension filled into soft gelatin capsules.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration. Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Each dosage unit for oral administration contains preferably from 1 to 250 mg (and for parenteral administration contains preferably from 01. to 25 mg) of a compound of the formula (I) or a pharmaceutically acceptable salt thereof calculated as the free base. The pharmaceutically acceptable compounds of the invention will normally be administered in a daily dosage regimen (for an adult patient) of, for example, an oral dose of from 1 mg to 500 mg, preferably between 10 mg and 400 mg, e.g. between 10 mg and 250 mg, or an intravenous, subcutaneous, or intramuscular dose of between 0.1 mg and 100 mg, preferably between 0.1 mg and 50 mg, e.g., between 1 mg and 25 mg, of the compound of formula (I) or a pharmaceutically acceptable salt, solvate or hydrate thereof calculated as the free base, the compound being administered 1 to 4 times per day. Suitably, the compounds will be administered for a period of continuous therapy, for example for a week or more.

Specific preferred compounds according to the present invention are given in Table 1 below, with reference to formula I.

TABLE 1

| R Chain Length | n | Group X | Group Y | Example |
|---|---|---|---|---|
| 4 | 1 | 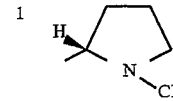 | phthalimido | 12b |
| 2 | 1 | 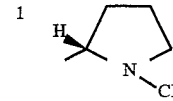 | phthalimido | 12f |
| 3 | 1 | 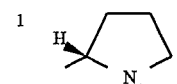 | phthalimido | 12d |
| 5 | 1 | 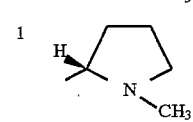 | phthalimido | 12e |
| 2 | 2 | —NH$_2$ | phthalimido | 13b |
| 3 | 2 | —NH$_2$ | phthalimido | 13c |
| 4 | 2 | —NH$_2$ | phthalimido | 13d |
| 5 | 2 | —NH$_2$ | phthalimido | 13e |
| 4 | 1 | 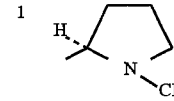 | phthalimido | 12k |
| 3 | 1 | 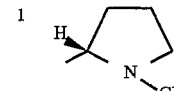 | sulfonimide | 12h |
| 4 | 1 | 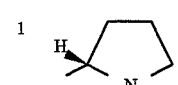 | benzosulfonimide | 12n |
| 6 | 1 | 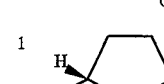 | benzosulfonimide | 12m |
| 3 | 2 | —NH$_2$ | benzosulfonimide | 13o |
| 4 | 2 | —NH$_2$ | benzosulfonimide | 13u |
| 6 | 2 | —NH$_2$ | benzosulfonimide | 13f |
| 4 | 1 | 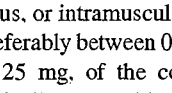 | naphthosultam | 12j |
| 6 | 1 | 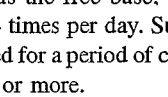 | naphthosultam | 12l |
| 3 | 1 | 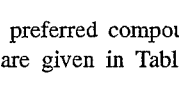 | naphthalimido | 12g |
| 4 | 1 |  | naphthalimido | 12i |
| 4 | 1 | 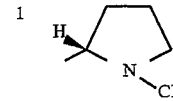 | naphthalimido | 12o |
| 3 | 2 | —NH$_2$ | naphthalimido | 13i |
| 4 | 2 | —NH$_2$ | naphthalimido | 13j |
| 5 | 2 | —NH$_2$ | naphthalimido | 13k |
| 4 | 1 | 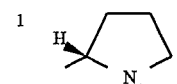 | naphthosultam | 12p |
| 3 | 2 | —NH$_2$ | naphthosultam | 13g |
| 4 | 2 | —NH$_2$ | naphthosultam | 13a |
| 6 | 2 | —NH$_2$ | naphthosultam | 13h |
| 3 | 2 | —N(CH$_3$)$_2$ | naphthosultam | 13t |
| 4(phenyl interrupted) | 2 | —NH$_2$ | naphthosultam | 13p |
| 4 branched | 2 | —NH$_2$ | naphthosultam | 13s |
| 5(phenyl interrupted) | 2 | —NH$_2$ | naphthosultam | 13q |
| 3 | 2 | —NH$_2$ | naphthalimido (2,3) | 13l |
| 4 | 2 | —NH$_2$ | tetrachlorophthalimido | 13m |
| 4 | 2 | —NH$_2$ | isoindolone | 14 |
| 5 | 2 | —NH$_2$ | camphorsultam | 13r |
| 4 | 1 | 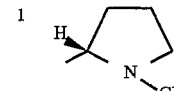 | bis-t-butyloxy-carbonylguanidino | 16 |
| 3 | 1 | 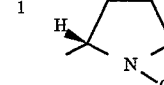 | carbobenzyloxy | 12c |
| 3 | 1 | 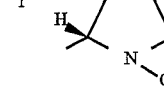 | t-butyloxycarbonyl | 12a |
| 3 | 2 | —NH$_2$ | 4-toluenesulfonamido | 13n |

TABLE 1-continued

| R Chain Length | n | Group X | Group Y | Example |
|---|---|---|---|---|
| 3 | 1 | (H-pyrrolidine-N-CH₃) | phthalimido | 12q |

EXAMPLE 1 (a)

3-(2-Benzyloxycarbonylpyrrolidin-2R-ylcarbonyl)-5-benzyloxy-1H-indole

To a stirred solution of N-benzyloxycarbonyl-R-proline (1 g, 4.01 mmol) in anhydrous methylene chloride (4 mL) was added oxalyl chloride (2M solution in methylene chloride, 3 mL, 6.02 mmol) and the resulting solution was stirred at room temperature under argon for 2 hours. The solvent was evaporated under reduced pressure and the crude product was washed three times with anhydrous hexanes and then evaporated to dryness to provide N-benzyloxycarbonyl-R-proline acid chloride which was used directly for the next reaction.

N-benzyloxycarbonyl-R-proline acid chloride from the above reaction was dissolved in anhydrous ether (13 mL) and was added dropwise at 0° C. to a stirred solution of 5-benzyloxyindole (0.716 g, 3.26 mmol) and t-butylmagnesium chloride (2M solution in diethyl ether, 3.55 mL, 7.06 mmol) in anhydrous diethyl ether (14 mL). The resulting reaction mixture was stirred at room temperature under argon for 45 minutes and then ethyl acetate (70 mL) and saturated sodium bicarbonate (15 mL) were added. The organic layer was dried and evaporated under reduced pressure to provide the title compound as a white solid (0.824 mg, 57.5%). m.p. 154°–156° C.

In a like manner, the following additional compound was prepared:
(b) 3-(2-Benzyloxycarbonylpyrrolidin-2S-ylcarbonyl)-5-benzyloxy-1H-indole, from N-benzyloxycarbonyl-S-proline.

EXAMPLE 2(a)

3-(N-methylpyrrolidin-2R-ylmethyl)-5-benzyloxy-1H-indole

To a solution of 3-(2-benzyloxycarbonylpyrrolidin-2R-ylcarbonyl)-5-benzyloxy-1H-indole (0.820 g, 1.80 mmol) in anhydrous tetrahydrofuran (7 mL) at 0° C. under argon, was added lithium aluminum hydride (1M solution in tetrahydrofuran, 14.5 mL, 14.5 mmol) and the resulting mixture was heated to reflux for 4 hours. The mixture was then cooled to 0° C. and quenched with water (1 mL) and ammonium hydroxide (7 mL) and then stirred at room temperature for 1 hour. The solution was then filtered through celite and the organic solvents were evaporated under reduced pressure. The crude product was extracted into methylene chloride (150 mL) and then evaporated to dryness. Purification was performed using silica gel chromatography with methylene chloride/ammonia (2M in methanol) (19:1) as the eluent to provide the title compound as a light yellow viscous oil (0.474 g, 82%). HRMS (FAB): MH⁺ for $C_{21}H_{24}N_2O$, calculated 321.1967, found 321.1949.

In a like manner, the following additional compound was prepared:

(b) 3-(N-methylpyrrolidin-2S-ylmethyl)-5-benzyloxy-1H-indole, from 3-(2-benzyloxycarbonylpyrrolidin-2S-ylcarbonyl)-5-benzyloxy-1H-indole; HRMS (FAB): MH⁺ for $C_{21}H_{24}N_2O$, calculated 321.1967, found 321.1972.

EXAMPLE 3(a)

3-(N-methylpyrrolidin-2R-ylmethyl)-5-hydroxy-1H-indole

A mixture of 3-(N-methylpyrrolidin-2R-ylmethyl)-5-benzyloxy-1H-indole (0.500 g, 1.56 mmol) and 10% palladium on charcoal (60 mg) was stirred in ethanol (20 mL) under an atmosphere of hydrogen overnight. The catalyst was removed by filtration through a bed of celite and the solvent was evaporated under reduced pressure. The residue was taken up in methylene chloride and filtered through a short silica gel column using methylene chloride/ammonia (2M in methanol) (9:1) as the eluent to provide the title compound as an off-white foam (0.355 g, 99%). m.p. 188°–189° C.; HRMS (FAB): MH⁺ for $C_{14}H_{18}N_2O$, calculated 231.149.7, found 231.1486.

In a like manner, the following additional compound as prepared:
(b) 3-(N-methylpyrrolidin-2S-ylmethyl)-5-hydroxy-1H-indole, from 3-(N-methylpyrrolidin-2S-ylmethyl)-5-benzyloxy-1H-indole; HRMS (FAB): MH⁺ for $C_{14}H_{18}N_2O$, calculated 231.1497, found 231.1501.

EXAMPLE 4

3-[2-(t-Butyloxycarbonylamino)ethyl]-5-hydroxy-1H-indole

To a solution of serotonin creatinine sulfate monohydrate (5.0 g, 12.3 mmol) in water (50 mL) was added di-t-butyl dicarbonate (3.0 g, 13.5 mmol) in tetrahydrofuran (30 mL) and the resulting mixture was stirred at room temperature overnight. The product was extracted into dichloromethane (3×50 mL) and the combined organic layers were washed with saturated sodium chloride (100 mL), dried over sodium sulfate and evaporated to dryness to provide the title compound as a colorless syrup (3.99 g, 100%).

EXAMPLE 5(a)

N-(3-Bromopropyl)-2,3-naphthalimide

To a solution of 2,3-naphthalimide (1.0 g, 5.1 mmol) in tetrahydrofuran (20 mL) at 0° C., were added 3-bromo-1-propanol (0.55 mL, 6.1 mmol), triphenylphosphine (2.66 g, 10.1 mmol) and diethyl azodicarboxylate (1.6 mL, 10.1 mmol). The reaction mixture was allowed to warm to room temperature, stirred overnight, evaporated to dryness and the product purified by silica gel chromatography using hexane/ethyl acetate (9:1 then 4:1) as eluent to provide the title compound as a powder (1.41 g, 87%).

In a like manner, the following additional compounds were prepared:
(b) N-(6-Bromohexyl)-2-benzoic sulfonimide, from 2-benzoic sulfonimide and 6-bromo-1-hexanol.
(c) N-(3-Bromopropyl)-1,8-naphthosultam, from 1,8-naphthosultam.
(d) N-(6-Bromohexyl)-1,8-naphthosultam, from 1,8-naphthosultam and 6-bromo-1-hexanol.
(e) N-(3-Bromopropyl)-1,8-naphthalimide, from 1,8-naphthalimide.
(f) N-(3-Bromopropyl)-N-(t-butyloxycarbonyl)-p-toluenesulfonamide, from N-(t-butyloxycarbonyl)-p-toluenesulfonamide.

EXAMPLE 6

N-(5-Bromopentyl)phthalimide

To a suspension n of phthalic anhydride (2.96 g, 20 mmol) in toluene (20 mL) was added 5-amino-1-pentanol (2.2 mL, 20 mmol) and the resulting mixture was heated to reflux for 14 hours. The solvent was removed under reduced pressure and the residue dissolved in dichloromethane (20 mL). This solution was cooled to 0° C. and triphenylphosphine (4.7 g, 18 mmol) and bromine were added. After warming to room temperature, the solution was stirred overnight and then poured into water (20 mL) and the organic phase was separated. The aqueous phase was extracted with dichloromethane (20 mL) and the combined organic phases were dried over sodium sulfate and evaporated to dryness. Silica gel chromatography using hexane/ethyl acetate (4:1) as the eluent gave the title compound as a syrup (4.13 g, 70% for 2 steps).

EXAMPLE 7(a)

3-[2-(t-Butyloxycarbonylamino)ethyl]-5-(4-bromo-1-methylpentyloxy)-1H-indole To a solution of 3-[2-(t-butyloxycarbonylamino)ethyl]-5-hydroxy-1H-indole (1.34 g, 4.86 mmol) in acetonitrile (50 mL) were added 2,5-dibromohexane (2.4 g, 9.72 mmol) and potassium carbonate (1.3 g, 9.72 mmol) and the resulting mixture was stirred at reflux for 60 hours. After cooling to room temperature, the solution was poured into ethyl acetate (40 mL), washed with water (40 mL), dried over sodium sulfate and evaporated to dryness. Column chromatography on silica gel using hexane/ethyl acetate (4:1, 2:1 and 1:1) provided the title compound as a syrup (0.65 g, 30%).

In a like manner, the following additional compounds were prepared:

(b) 3-[2-(t-Butyloxycarbonylamino)ethyl]-5-(3-bromopropyloxy)-1H-indole, from 1,3-dibromopropane.

(c) 3-[2-(t-Butyloxycarbonylamino)ethyl]-5-[(2-bromomethyl)benzyloxy]-1H-indole, from α,α'-dibromo-o-xylene.

(d) 3-[2-(t-Butyloxycarbonylamino)ethyl]-5-[(3-bromomethyl)benzyloxy]-1H-indole, from α,α'-dibromo-m-xylene.

(e) 3-[2-(t-Butyloxycarbonylamino)ethyl]-5-(5-bromopentyloxy)-1H-indole, from 1,5-dibromopentane.

(f) 3-[2-(t-Butyloxycarbonylamino)ethyl]-5-(4-bromobutyloxy)-1H-indole, from 1,4-dibromobutane.

EXAMPLE 8

3-(2-N,N-Dimethylaminoethyl)-5-hydroxy-1H-indole

To a solution of 3-[2-(t-butyloxycarbonylamino)ethyl]-5-hydroxy-1H-indole (3.55 g, 12.8 mmol) in tetrahydrofuran (150 mL) cooled to 0° C. was added lithium aluminum hydride (4.9 g, 128 mmol) portionwise. The resulting mixture was heated to reflux for 3 hours, cooled to 0° C., quenched with water (30 mL) and filtered through celite (rinsing with ethyl acetate and water). To the filtrate were added di-t-butyl dicarbonate (2.75 g, 12.6 mmol) and potassium carbonate (5 g, 36.2 mmol) and the resulting mixture was stirred overnight at room temperature. The organic phase was separated, washed with water and evaporated to dryness. This residue was dissolved in tetrahydrofuran (100 mL), cooled to 0° C. and lithium aluminum hydride (4.9 g, 128 mmol) was added slowly. The resulting mixture was heated to reflux for 3 hours, cooled to 0° C. and quenched with water (30 mL). The solution was then filtered though celite and rinsed with methanol and evaporated to dryness. Column chromatography on silica gel using ethyl acetate/methanol/ammonium hydroxide (40:10:1) as the eluent provided the title compound as a syrup (0.5 g, 19% for 2 steps).

EXAMPLE 9

N-(Carbobenzyloxy)-1-bromo-3-propylamine

To a stirred solution of 1-bromo-3-propylamine hydrobromide (5 g, 22.84 mmol) in saturated aqueous sodium carbonate (100 mL) and ethyl acetate (200 mL) at 0° C., was added benzylchloroformate (3.2 mL, 22.84 mmol) and the resulting mixture was warmed to room temperature and stirred overnight. The aqueous layer was separated and extracted with ethyl acetate (2×100 mL) and the combined organic layers were washed with brine (2×100 mL), dried over sodium sulfate and evaporated to dryness under reduced pressure. Silica gel chromatography using ethyl acetate/hexanes (1:9) provided the title compound as a colorless oil (4.7 g, 79%).

EXAMPLE 10

N-(t-Butyloxycarbonyl)-1-bromo-3-propylamine

To a stirred solution of 1-bromo-3-propylamine hydrobromide (5 g, 22.84 mmol) in chloroform (150 mL) at 0° C. was added saturated aqueous sodium carbonate (100 mL) and di-t-butyl dicarbonate (4.9 g, 22.84 mmol) and the resulting mixture was warmed to room temperature and stirred for 4 hours. The aqueous layer was separated and extracted with dichloromethane (2×100 mL) and the combined organic layers were washed with brine (2×100 mL), dried over sodium sulfate and evaporated to dryness under reduced pressure. Silica gel chromatography using ethyl acetate/hexanes (1:9) provided the title compound as a colorless oil (5.6 g, 90%).

EXAMPLE 11(a)

N-(4-Bromobutyl)-1,8-naphthalimide

To a solution of sodium hydride (1.3 g, 55.48 mmol) in anhydrous tetrahydrofuran (150 mL) at 0° C. under argon, was added a solution of 1,4-butanediol (5 g, 55.48 mmol) in anhydrous tetrahydrofuran (50 mL). The resulting mixture was stirred at room temperature for 45 minutes over which time a large amount of a white precipitate formed. t-Butyldimethylsilyl chloride (8.3 g, 55.48 mmol) was then added and the resulting mixture was stirred vigorously for 45 minutes and then diluted with diethyl ether (200 mL) and filtered. The filtrate was washed with 10% aqueous potassium carbonate (25 mL) and brine (2×50 mL). Purification by silica gel chromatography using hexane/ethyl acetate as eluent (7:3) gave 1-t-butyldimethylsilyloxy-4-hydroxybutane as a colorless oil (9.2 g, 80%). 1-t-Butyldimethylsilyloxy-4-hydroxybutane (2.0 g, 9.85 mmol), triphenylphosphine (3.07 g, 11.74 mmol) and diethyl azodicarboxylate (1.8 mL, 11.74 mmol) were added successively to a solution of 1,8-naphthalimide (1.92 g, 9.785 mmol) in anhydrous tetrahydrofuran (50 mL) at 0° C. under an atmosphere of argon. The reaction was allowed to warm to room temperature and stirred overnight. After removing the solvent under reduced pressure, the product was purified by silica gel chromatography using hexane/ethyl acetate (9:1) as the eluent to provide 4-t-butyldimethylsilyloxybutyl-1,8 naphthalimide as a colorless oil (3.68 g, 87%).

To a stirred solution of 4-t-butyldimethylsilyloxybutyl-1,8 naphthalimide (3.0 g, 8.34 mmol) in methanol (42 mL) was added a catalytic amount of p-toluenesulfonic acid (0.317 g, 1.7 mmol) and the resulting mixture was stirred at room temperature for 10 minutes. The solution was diluted with ethyl acetate (150 mL) and washed with saturated sodium bicarbonate solution (2×15 mL) and brine (2×20 mL). The organic layer was dried over sodium sulfate and evaporated to dryness to obtain 4-hydroxybutyl-1,8 naphthalimide as a colorless oil (2.3 g, 100%).

A solution of bromine (0.252 mL, 4.90 mmol) in anhydrous dichloromethane (10 mL) was added dropwise to a solution of triphenylphosphine (1.28 g, 4.90 mmol) in anhydrous dichloromethane (2 mL) at 0° C. under argon. After stirring for 10 minutes, a solution of 4-hydroxybutyl-1,8 naphthalimide (1.1 g, 4.08 mmol) in anhydrous dichloromethane (10 mL) was added and the resulting mixture was allowed to warm to room temperature and the reaction monitored by thin layer chromatography. Once all of the starting material had been consumed (~4 hours), the mixture was diluted with ethyl acetate (200 mL) and washed with saturated sodium bicarbonate (2×10 mL) and brine (2×15 mL), dried over sodium sulfate and evaporated to dryness. The product was purified by silica gel chromatography using hexane/ethyl acetate (9:1) as the eluent to provide the title compound as a white solid (0.817 g, 60.5%). m.p. 146°–148° C.

In a like manner, the following additional compounds were prepared:
(b) N-(4-Bromobutyl)-1,8-naphthosultam, from 1,8-naphthosultam.
(c) N-(4-Bromobutyl)-2-benzoic sulfonimide, from 2-benzoic sulfonimide.

EXAMPLE 12

General alkylation procedure A

To a solution of 3-[N-methylpyrrolidin-2(R or S)-ylmethyl]-5-hydroxy-1H-indole (1 eq) in anhydrous acetonitrile (0.2M) at room temperature under argon were added solid potassium carbonate (5 eq) and the appropriate alkyl bromide (1.2 eq). The resulting mixture was heated to reflux for 12 hours. The reaction was cooled to room temperature, filtered and quenched with water (5 mL). The product was extracted into methylene chloride (3×25 mL) and the organic layers dried over sodium sulfate and evaporated to dryness. Purification by silica gel chromatography using chloroform/ammonia (2M in methanol) (~30:1 to 9:1) provided the desired compounds (40 to 85%).

Using the above procedure, the following compounds were prepared:
(a) 3-(N-Methylpyrrolidin-2S-ylmethyl)-5-[N-(t-butyloxycarbonyl)-3-aminopropyloxy)-1H-indole, from N-(t-butyloxy-carbonyl)-1-bromo-3-propylamine and 3-(N-methylpyrrolidin-2S-ylmethyl)-5-hydroxy-1H-indole; light yellow viscous oil; HRMS (FAB): MH$^+$ for $C_{22}H_{33}N_3O_3$, calculated 388.2600, found 388.2589.
(b) 3-(N-Methylpyrrolidin-2S-ylmethyl)-5-(4-phthalimidobutyloxy)-1H-indole, from N-(4-bromobutyl) phthalimide and 3-(N-methylpyrrolidin-2S-ylmethyl)-5-hydroxy-1H-indole; light yellow viscous oil; HRMS (FAB): MH$^+$ for $C_{26}H_{29}N_3O_3$, calculated 432.2287, found 432.2290.
(c) 3-(N-Methylpyrrolidin-2S-ylmethyl)-5-[N-(carbobenzyloxy)-3-aminopropyloxy]-1H-indole from N-(carbobenzyloxy)-1-bromo-3-propylamine and 3-(N-methylpyrrolidin-2S-ylmethyl)-5-hydroxy-1H-indole; yellow viscous oil; HRMS (FAB): MH$^+$ for $C_{25}H_{31}N_3O_3$, calculated 422.2444, found 422.2428.
(d) 3-(N-Methylpyrrolidin-2S-ylmethyl)-5-(3-phthalimidopropyloxy)-1H-indole, from N-(3-bromopropyl)phthalimide and 3-(N-methylpyrrolidin-2S-ylmethyl)-5-hydroxy-1H-indole; yellow viscous oil; HRMS (FAB): MH$^+$ for $C_{25}H_{27}N_3O_3$, calculated 418.2131, found 418.2122.
(e) 3-(N-Methylpyrrolidin-2S-ylmethyl)-5-(5-phthalimidopentyloxy)-1H-indole, from N-(5-bromopentyl)phthalimide and 3-(N-methylpyrrolidin-2S-ylmethyl)-5-hydroxy-1H-indole; yellow viscous oil; HRMS (FAB): MH$^+$ for $C_{27}H_{31}N_3O_3$, calculated 446.2444, found 446.2451.
(f) 3-(N-Methylpyrrolidin-2S-ylmethyl)-5-(2-phthalimidoethyloxy)-1H-indole, from N-(2-bromoethyl) phthalimide and 3-(N-methylpyrrolidin-2S-ylmethyl)-5-hydroxy-1H-indole; yellow powder; m.p. 58°–60° C.; HRMS (FAB): MH$^+$ for $C_{24}H_{28}N_3O_3$, calculated 404.1974, found 404.1979.
(g) 3-(N-Methylpyrrolidin-2S-ylmethyl)-5-[3-(1,8-naphthalimido)propyloxy]-1H-indole, from N-(3-bromopropyl)-1,8-naphthalimide and 3-(N-methylpyrrolidin-2S-ylmethyl)-5-hydroxy-1H-indole; light yellow foam; m.p. 58°–60° C.; HRMS (FAB): MH$^+$ for $C_{29}H_{29}N_3O_3$, calculated 468.2287, found 468.2274.
(h) 5-[3-(2-Benzoicsulfonimido)propyloxy]-3-(N-methylpyrrolidin-2S-ylmethyl)-1H-indole, from N-(3-bromopropyl)-2-benzoic sulfonimide and 3-(N-methylpyrrolidin-2S-ylmethyl)-5-hydroxy-1H-indole; colorless viscous oil; HRMS (FAB): MH$^+$ for $C_{24}H_{27}N_3SO_4$, calculated 454.1801, found 454.1798.
(i) 3-(N-Methylpyrrolidin-2S-ylmethyl)-5-[4-(1,8-naphthalimido)butyloxy]-1H-indole, from N-(4-bromobutyl)-1,8-naphthalimide and 3-(N-methylpyrrolidin-2S-ylmethyl)-5-hydroxy-1H-indole; yellow oil; HRMS (FAB): MH$^+$ for $C_{30}H_{31}N_3O_3$, calculated 482.2444, found 482.2442.
(j) 3-(N-Methylpyrrolidin-2S-ylmethyl)-5-[4-(1,8-naphthosultam-N-yl)butyloxy]-1H-indole, from N-(4-bromobutyl)-1,8-naphthosultam and 3-(N-methylpyrrolidin-2S-ylmethyl)-5-hydroxy-1H-indole; yellow oil; HRMS (FAB): MH$^+$ for $C_{28}H_{31}N_3SO_3$, calculated 490.2152, found 490.2148.
(k) 3-(N-Methylpyrrolidin-2R-ylmethyl)-5-(4-phthalimidobutyloxy)-1H-indole, from N-(4-bromobutyl) phthalimide and 3-(N-methylpyrrolidin-2R-ylmethyl)-5-hydroxy-1H-indole; yellow viscous oil; HRMS (FAB): MH$^+$ for $C_{26}H_{29}N_3O_3$, calculated 432.2287, found 432.2277.
(l) 3-(N-Methylpyrrolidin-2S-ylmethyl)-5-[6-(1,8-naphthosultam-N-yl)hexyloxy]-1H-indole, from N-(6-bromohexyl)-1,8-naphthosultam and 3-(N-methylpyrrolidin-2S-ylmethyl)-5-hydroxy-1H-indole; yellow oil; HRMS (FAB): MH$^+$ for $C_{30}H_{35}N_3SO_3$, calculated 518.2477, found 518.2466.
(m) 5-[6-(2-Benzoicsulfonimido)hexyloxy]-3-(N-methylpyrrolidin-2S-ylmethyl)-1H-indole, from N-(6-bromohexyl)-2-benzoic sulfonimide and 3-(N-methylpyrrolidin-2S-ylmethyl)-5-hydroxy-1H-indole; yellow oil.
(n) 5-[4-(2-Benzoicsulfonimido)butyloxy]-3-(N-methylpyrrolidin-2S-ylmethyl)-1H-indole, from N-(4-bromobutyl)-2-benzoic sulfonimide and 3-(N-methylpyrrolidin-2S-ylmethyl)-5-hydroxy-1H-indole; yellow foam; m.p. 68°–70° C.; HRMS (FAB): MH$^+$ for $C_{25}H_{29}N_3SO_4$, calculated 468.1957, found 468.1953.

(o) 3-(N-Methylpyrrolidin-2R-ylmethyl)-5-[4-(1,8-naphthalimido)butyloxy]-1H-indole, from N-(4-bromobutyl)-1,8-naphthalimide and 3-(N-methylpyrrolidin-2R-ylmethyl)-5-hydroxy-1H-indole; yellow viscous oil; HRMS (FAB): M$^+$ for $C_{30}H_{32}N_3O_3$, calculated 482.2443, found 482.2443.

(p) 3-(N-Methylpyrrolidin-2R-ylmethyl)-5-[4-(1,8-naphthosultam-N-yl)butyloxy]-1H-indole, from N-(4-bromobutyl)-1,8-naphthosultam and 3-(N-methylpyrrolidin-2R-ylmethyl)-5-hydroxy-1H-indole; light yellow viscous oil; HRMS (FAB): MH$^+$ for $C_{28}H_{31}N_3SO_3$, calculated 490.2164, found 490.2162.

(q) 3-(N-Methylpyrrolidin-2R-ylmethyl)-5-(3-phthalimidopropyloxy)-1H-indole, from N-(3-bromopropyl)phthalimide and 3-(N-methylpyrrolidin-2R-ylmethyl)-5-hydroxy-1H-indole; yellow viscous oil; HRMS (FAB): MH$^+$ for $C_{25}H_{27}N_3O_3$, calculated 418.2131, found 418.2130.

EXAMPLE 13

General alkylation procedure B

3-[2-(t-Butyloxycarbonylamino)ethyl]-5-hydroxy-1H-indole (1 eq), alkyl bromide (1.2 eq) and potassium carbonate (2.5 eq) were mixed in acetonitrile (0.02M) and stirred at reflux for 20 hours. The mixture was then poured into ethyl acetate (30 mL), washed with water (30 mL), dried over sodium sulfate and evaporated to dryness. Column chromatography on silica gel using hexanes/ethyl acetate as eluent gave the desired alkylated compound as a syrup (37–90%). Removal of the N-t-butyloxycarbonyl protecting group was then performed by dissolving the alkylated product in 3N HCl in ethyl acetate (3 mL) and stirring at room temperature for 15 minutes. Evaporation of the solvent under reduced pressure gave the hydrochloride salts of the title compounds as foams (100%).

Using the above procedure, the following compounds were prepared:

(a) 3-(2-Aminoethyl)-5-[4-(1,8-naphthosultam-N-yl)butyloxy]-1H-indole, from N-(4-bromobutyl)-1,8-naphthosultam.

(b) 3-(2-Aminoethyl)-5-(2-phthalimidoethyloxy)-1H-indole, from N-(2-bromoethyl)phthalimide.

(c) 3-(2-Aminoethyl)-5-(3-phthalimidopropyloxy)-1H-indole, from N-(3-bromopropyl)phthalimide.

(d) 3-(2-Aminoethyl)-5-(4-phthalimidobutyloxy)-1H-indole, from N-(4-bromobutyl)phthalimide.

(e) 3-(2-Aminoethyl)-5-(5-phthalimidopentyloxy)-1H-indole, from N-(5-bromopentyl)phthalimide.

(f) 3-(2-Aminoethyl)-5-[6-(2-benzoic sulfonimido)hexyloxy]-1H-indole, from N-(6-bromohexyl)-2-benzoic sulfonimide.

(g) 3-(2-Aminoethyl)-5-[3-(1,8-naphthosultam-N-yl)propyloxy]-1H-indole, from N-(3-bromopropyl)-1,8-naphthosultam.

(h) 3-(2-Aminoethyl)-5-[6-(1,8-naphthosultam-N-yl)hexyloxy]-1H-indole, from N-(6-bromohexyl)-1,8-naphthosultam.

(i) 3-(2-Aminoethyl)-5-[3-(1,8-naphthalimido)propyloxy]-1H-indole, from N-(3-bromopropyl)-1,8-naphthalimide.

(j) 3-(2-Aminoethyl)-5-[4-(1,8-naphthalimido)butyloxy]-1H-indole, from N-(4-bromobutyl)-1,8-naphthalimide.

(k) 3-(2-Aminoethyl)-5-[5-(1,8-naphthalimido)pentyloxy]-1H-indole, from 1,8-naphthalimide and 3-[2-(t-butyloxycarbonylamino)ethyl]-5-(5-bromopentyloxy)-1H-indole.

(l) 3-(2-Aminoethyl)-5-[3-(2,3-naphthalimido)propyloxy]-1H-indole, from N-(3-bromopropyl)-2,3-naphthalimide.

(m) 3-(2-Aminoethyl)-5-[4-(tetrachlorophthalimido)butyloxy]-1H-indole, from tetrachlorophthalimide and 3-[2-(t-butyloxycarbonylamino)ethyl]-5-(4-bromobutyloxy)-1H-indole.

(n) 3-(2-Aminoethyl)-5-[3-(4-toluenesulfonamido)propyloxy]-1H-indole, from N-(3-bromopropyl)-N-(t-butyloxycarbonyl)-p-toluenesulfonamide.

(o) 3-(2-Aminoethyl)-5-[3-(2-benzoic sulfonimido)propyloxy]-1H-indole, from 2-benzoic sulfonimide and 3-[2-(t-butyloxycarbonylamino)ethyl]-5-(3-bromopropyloxy)-1H-indole.

(p) 3-(2-Aminoethyl)-5-[2-(1,8-naphthosultam-N-methyl)benzyloxy]-1H-indole, from 1,8-naphthosultam and 3-[2-(t-butyloxycarbonylamino)ethyl]-5-[-(2-bromomethyl)benzyloxy]-1H-indole.

(q) α-[3-(2-Aminoethyl)-1H-indol-5-yloxy]-α'-(1,8-naphthosultam-N-yl)-m-xylene, from 1,8-naphthosultam and 3-[2-(t-butyloxycarbonylamino)ethyl]-5-[-(3-bromomethyl)benzyloxy]-1H-indole.

(r) 3-(2-Aminoethyl)-5-[5-(1S-2,10-camphorsultam-N-yl)pentyloxy]-1H-indole, from 1S-2,10-camphorsultam and 3-[2-(t-butyloxycarbonylamino)ethyl]-5-(5-bromopentyloxy)-1H-indole.

(s) 3-(2-Aminoethyl)-5-[1-methyl-4-(1,8-naphthosultam-N-yl)pentyloxy]-1H-indole, from 1,8-naphthosultam and 3-[2-(t-butyloxycarbonylamino)ethyl]-5-(4-bromo-1-methylpentyloxy)-1H-indole.

(t) 3-(2-N,N-Dimethylaminoethyl)-5-[3-(1,8-naphthosultam-N-yl)propyloxy]-1H-indole, from N-(3-bromopropyl)-1,8-naphthosultam and 3-(2-N,N-dimethylaminoethyl)-5-hydroxy-1H-indole.

(u) 3-(2-aminoethyl)-5-[4-(2-benzoic sulfonimido)butyloxy]-1H-indole, from 2-benzoic sulfonimide and 3-[2-(t-butyloxycarbonylamino)ethyl]-5-(4-bromobutyloxy)-1H-indole.

EXAMPLE 14

3-(2-Aminoethyl)-5-[4-(3-hydroxyisoindolin-1-on-2-yl)butyloxy]-1H-indole

To a solution of 3-(2-aminoethyl)-5-(4-phthalimidobutyloxy)-1H-indole hydrochloride (0.057 g, 0.14 mmol) in methanol (10 mL) was added sodium borohydride (0.057 g, 1.36 mmol) and the resulting mixture was stirred at room temperature for 4 hours. The solution was then poured onto a silica gel column and the product eluted with methanol/ammonium hydroxide (19:1) to give the title compound as a syrup (0.052 g, 100%).

EXAMPLE 15

3-(N-Methylpyrrolidin-2S-ylmethyl)-5-(4-aminobutyloxy)-1H-indole

To a solution of 3-(N-methylpyrrolidin-2S-ylmethyl)-5-(4-phthalimidobutyloxy)-1H-indole (0.225 g, 0.521 mmol) in ethanol/dichloromethane (1:1, 6 mL), was added hydrazine hydrate (0.126 mL, 2.605 mmol) and the resulting mixture was stirred at room temperature overnight. The solution was filtered and the filtrate evaporated to dryness and the crude product purified by silica gel chromatography using chloroform/ammonia (2M in methanol) (17:3) as the eluent to provide the title compound as a yellow oil (0.098 g, 62%). HRMS (FAB): MH$^+$ for $C_{18}H_{27}N_3O$, calculated 302.2232, found 302.2239.

EXAMPLE 16

3-(N-Methylpyrrolidin-2S-ylmethyl)-5-[4-(bis-t-butyloxycarbonylguanadino)butyloxy]-1H-indole To a solution of 3-(N-methylpyrrolidin-2S-ylmethyl)-5-(4-aminobutyloxy)-1H-indole (0.075 g, 0.248 mmol) in anhydrous dimethylformamide (1.2 mL) at room temperature, was added triethylamine (0.173 mL, 1.240 mmol) and the resulting solution was stirred for 10 minutes before a solution of bis-(t-butyloxycarbonyl)thiourea (0.076 g, 1.273 mmol) in dimethylformamide (1 mL) was added. The reaction was then allowed to stir at room temperature for 16 hours. Methylene chloride (3 mL) and water (2 mL) were added and the organic phase was separated and the aqueous phase was extracted with dichloromethane (3×15 mL). The combined organic layers were washed with water (2×5 mL) and brine (2×5 mL), dried over sodium sulfate and evaporated to dryness. Purification by silica gel chromatography using chloroform/ammonia (2M in methanol) (19:1) provided the title compound as a yellow oil. HRMS (FAB): $MH^+$ for $C_{29}H_{45}N_5O_5$, calculated 544.3499, found 544.3513

EXAMPLE 17

Comparison of Binding Affinities

Compounds of the previous examples, as well as reference compounds, were evaluated for binding affinity using cell types receptive specifically to $5\text{-HT}_{1D\alpha}$ and $5\text{-HT}_{1a}$ ligands. The assay protocol generally entailed the incubation of membranes prepared from cells expressing the $1d\alpha$ subtype of 5-HT receptors, with $^3$H-5-HT and membranes prepared from cells expressing the $5\text{-HT}_{1A}$ subtype, with 8-hydroxy-[$^3$H]-DPAT. Increasing concentrations of the test compound were incubated with the radioligand and the membrane homogenates prepared from the recombinant cells. After a 60 minute incubation at 22° C. for $5\text{-HT}_{1D\alpha}$ and 15 minutes at 37° C. for $5\text{-HT}_{1A}$, the incubation was terminated by vacuum filtration. The filters were washed with buffer and counted for radioactivity using liquid scintillation spectrometry. The affinity of the test compound for $5\text{-HT}_{1D}$ receptors was determined by computer-assisted analysis of the data and by determining the amount of the compound necessary to inhibit 50% of the binding of the radioligand to the receptor. Concentrations ranging from $10^{-11}$M to $10^{-5}$M of the test compounds were evaluated. For comparison, sumatriptan, the previously mentioned prior art compound, was also evaluated. The results are presented in Table 2 below, with reference to the above specific examples

TABLE 2

| Example | $K_I$ (nm) $5\text{-HT}_{1D\alpha}$ | $5\text{-HT}_{1A}$ | Ratio, $5HT_{1A}$ $5HT_{1D\alpha}$ |
| --- | --- | --- | --- |
| 12b | 0.60 | (482) | 803 |
| 12d | 53 | 368 | 7 |
| 12e | 7.85 | 218 | 28 |
| 13c | 7.3 | 14 | 2 |
| 13d | 0.21 | 30 | 143 |
| 13f | 0.39 | 4.8 | 12 |
| 13g | 1.5 | 7.2 | 5 |
| 13a | 0.68 | 206 | 303 |
| 16 | 21.8 | 80.9 | 4 |
| 12c | 15.7 | 21.7 | 1.4 |
| 12a | 83.4 | 103 | 1.2 |
| sumatriptan | 5.3 | 307.4 | 58 |

What is claimed is:

1. A 5-Alkoxy-tryptamine compound exhibiting selectivity towards 5-HT receptors of brain cells, and corresponding to general formula I:

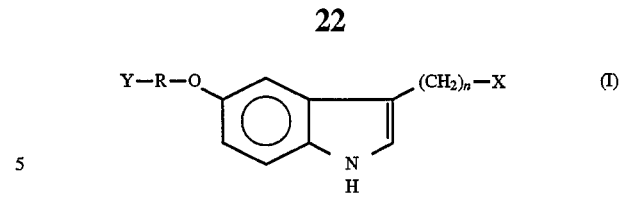

wherein n is an integer from 1–3;

R represents a straight or branched $C_1$–$C_9$ alkylene chain optionally interrupted by a phenylene group; —X represents amino, mono(loweralkyl)amino, di(loweralkyl) amino or optionally N-lower alkyl-substituted pyrrolidine;

and Y represents optionally substituted phthalimide, benzosulfonimide, naphthosultam, naphthalimide, isoindolone, camphorsultam, toluenesulfonamido, N,N'-dicarboxylated guanidino or N-carboxylated amino, each of which is linked to R via a respective N-group thereof.

2. A 5-Alkoxy-tryptamine compound of formula I as claimed in claim 1 in which integer n is 1 or 2.

3. A 5-Alkoxy-tryptamine compound of formula 1 as claimed in claim 2 in which R is an alkylene group of from 2 to 6 carbon atoms, optionally interrupted by a phenylene group.

4. A 5-Alkoxy-tryptamine compound of formula I as claimed in claim 3 in which R is n-butylene.

5. A 5-Alkoxy-tryptamine compound according to claim 1 wherein X represents pyrrolidine bonded through a methylene group of the pyrrolidine ring.

6. A 5-Alkoxy-tryptamine compound according to claim 5 wherein the N-group of the pyrrolidine ring is substituted with lower alkyl.

7. A 5-Alkoxy-tryptamine compound according to claim 1 wherein X represents pyrrolidine bonded through its N-group.

8. A 5-Alkoxy-tryptamine compound according to claim 1 wherein Y represents phthalimido optionally substituted on its benzene ring with up to 4 halogen groups.

9. A 5-Alkoxy-tryptamine compound according to claim 1 wherein Y represents benzosulfonimide.

10. A 5-Alkoxy-tryptamine compound according to claim 1 wherein Y represents naphthosultam.

11. A 5-Alkoxy-tryptamine compound according to claim 1 wherein Y represents naphthalimide.

12. A 5-Alkoxtryptamine compound according to claim 1 wherein Y represents isoindolone.

13. A 5-Alkoxy-tryptamine compound according to claim 1 wherein Y represents camphorsultam.

14. A 5-Alkoxy-tryptamine compound according to claim 1 wherein Y represents toluenesulfonamido.

15. A 5-Alkoxy-tryptamine compound according to claim 1 wherein Y represents carboxylated guanidino.

16. A 5-Alkoxy-tryptamine compound according to claim 1 wherein Y represents N-carboxylated amino.

17. A 5-alkoxy-tryptamine compound according to claim 1 which is 5-[3-(2-benzoicsulfinimido)propyloxy]-3-(N-methylpyrrolidin-2S-ylmethyl)-1H-indole.

18. A 5-alkoxy-tryptamine compound according to claim 1 which is 5-[4-(2-benzoicsulfinimido)butyloxy]-3-(N-methylpyrrolidin-2S-ylmethyl)-1H-indole.

19. A 5-alkoxy-tryptamine compound according to claim 1 which is 5-[6-(2-benzoicsulfinimido)hexyloxy]-3-(N-methylpyrrolidin-2S-ylmethyl)-1H-indole.

20. A 5-alkoxy-tryptamine compound according to claim 1 which is 3-(N-methylpyrrolidin-2S-ylmethyl)-5-[4-(1,8-naphthsultam-N-yl)butyloxy]-1H-indole.

21. A 5-alkoxy-tryptamine compound according to claim 1 which is 3-(N-methylpyrrolidin-2R-ylmethyl)-5-[4-(1,8-naphthosultam-N-yl)butyloxy]-1H-indole.

22. A 5-alkoxy-tryptamine compound according to claim 1 which is 3-(N-methylpyrrolidin-2S-ylmethyl)-5-[6-(1,8-naphthosultam-N-yl)hexyloxy]-1H-indole.

23. A 5-alkoxy-tryptamine compound according to claim 1 which is 3-(N-methylpyrrolidin-2S-ylmethyl)-5-[3-(1,8-naphthalimido)propyloxy]-1H-indole.

24. A 5-alkoxy-tryptamine compound according to claim 1 which is 3-(N-methylpyrrolidin-2S-ylmethyl)-5-[4-(1,8-naphthalimido)butyloxy]-1H-indole.

25. A 5-alkoxy-tryptamine compound according to claim i which is 3-(N-methylpyrrolidin-2R-ylmethyl)-5-[4-(1,8-naphthalimido)butyloxy]-1H-indole.

26. A 5-alkoxy-tryptamine compound according to claim 1 which is 3-(N-methylpyrrolidin-2S-ylmethyl)-5-(2-phthalimidoethyloxy)-1H-indole.

27. A 5-alkoxy-tryptamine compound according to claim 1 which is 3-(N-methylpyrrolidin-2S-ylmethyl)-5-(2-phthalimidopropyloxy)-1H-indole.

28. A 5-alkoxy-tryptamine compound according to claim 1 which is 3-(N-methylpyrrolidin-2S-ylmethyl)-5-(4-phthalimidobutyloxy)-1H-indole.

29. A 5-alkoxy-tryptamine compound according to claim 1 which is 3-(N-methylpyrrolidin-2R-ylmethyl)-5-(4-phthalimidobutyloxy)-1H-indole.

30. A 5-alkoxy-tryptamine compound according to claim 1 which is 3-(N-methylpyrrolidin-2S-ylmethyl)-5-(5-phthalimidpentyloxy)-1H-indole.

31. A 5-alkoxy-tryptamine compound according to claim 1 which is 3-(2-aminoethyl)-5-(3-phthalimidopropyloxy)-1H-indole.

32. A 5-alkoxy-tryptamine compound according to claim 1 which is 3-(2-aminoethyl)-5-(4-phthalimidobutyloxy)-1H-indole.

33. A 5-alkoxy-tryptamine compound according to claim 1 which is 3-(2-aminoethyl)-5-(5-phthalimidopentyloxy)-1H-indole.

34. A 5-alkoxy-tryptamine compound according to claim 1 which is 3-(2-aminoethyl)-5-(2-phthalimidoethyloxy)-1H-indole.

35. A 5-alkoxy-tryptamine compound according to claim 1 which is 3-(2-aminoethyl)-5-[3-(2-benzoic sulfinimido)propyloxy]-1H-indole.

36. A 5-alkoxy-tryptamine compound according to claim 1 which is 3-(2-aminoethyl)-5-[4-(2-benzoic sulfinimido)butyloxy]-1H-indole.

37. A 5-alkoxy-tryptamine compound according to claim 1 which is 3-(2-aminoethyl)-5-[6-(2-benzoic sulfinimido)hexyloxy]-1H-indole.

38. A 5-alkoxy-tryptamine compound according to claim 1 which is 3-(2-aminoethyl)-5-[3-(1,8-naphthosultam-N-yl)propyloxy]-1H-indole.

39. A 5-alkoxy-tryptamine compound according to claim 1 which is 3-(2-aminoethyl)-5-[4-(1,8-naphthosultam-N-yl)butyloxy]-1H-indole.

40. A 5-alkoxy-tryptamine compound according to claim 1 which is 3-(2-aminoethyl)-5-[6-(1,8-naphthosultam-N-yl)hexyloxy]-1H-indole.

41. A 5-alkoxy-tryptamine compound according to claim 1 which is 3-(2-N,N-dimethylaminoethyl)-5-[3-(1,8-naphthosultam-N-yl)propyloxy]-1H-indole.

42. A 5-alkoxy-tryptamine compound according to claim 1 which is 3-(2-aminoethyl)-5-[3-(1,8-naphthalimido)propyloxy]-1H -indole.

43. A 5-alkoxy-tryptamine compound according to claim 1 which is 3-(2-aminoethyl)-5-[4-(1,8-naphthalimido)butyloxy]-1H-indole.

44. A 5-alkoxy-tryptamine compound according to claim 1 which is 3-(2-aminoethyl)-5-[5-(1,8-naphthalimido)pentyloxy]-1H-indole.

45. A 5-alkoxy-tryptamine compound according to claim 1 which is 3-(2-aminoethyl)-5-[2-(1,8-naphthosultam-N-methyl)benzyloxy]-1H-indole.

46. A 5-alkoxy-tryptamine compound according to claim 1 which is 3-(2-aminoethyl)-5-[1-methyl-4-(1,8-naphthosultam-N-yl)pentyloxy]-1H-indole.

47. A 5-alkoxy-tryptamine compound according to claim 1 which is α-[3-(2-aminoethyl)-1H-indol-5-yloxy]-α'-(1,8-naphthosultam-N-yl)-m-xylene.

48. A 5-alkoxy-tryptamine compound according to claim 1 which is 3-(2-aminoethyl)-5-[3-(2,3-naphthalimido)propyloxy]-1H-indole.

49. A 5-alkoxy-tryptamine compound according to claim 1 which is 3-(2-aminoethyl)-5-[4-(tetrachlorophthalimido)butyloxy]-1H-indole.

50. A 5-alkoxy-tryptamine compound according to claim 1 which is 3-(2-aminoethyl)-5-[4-(3-hydroxyisoindolin-1-on-2-y)butyloxy]-1H-indole.

51. A 5-alkoxy-tryptamine compound according to claim 1 which is 3-(2-aminoethyl)-5-[5-(1S-2,10-camphorsultam-N-yl)pentyloxy]-1H-indole.

52. A 5-alkoxy-tryptamine compound according to claim 1 which is 3-(2-aminoethyl)-5-[3-(4-toluenesulfonamido)propyloxy]-1H-indole.

53. A 5-alkoxy-tryptamine compound according to claim 1 which is 3-(N-methylpyrrolidin-2S-ylmethyl)-5-[4-(bis-t-butyloxycarbonylguanidino)butyloxy]-1H-indole.

54. A 5-alkoxy-tryptamine compound according to claim 1 which is 3-(N-methylpyrrolidin-2S-ylmethyl)-5-[N-(carbobenzyloxy)-3-aminopropyloxy]-1H-indole.

55. A 5-alkoxy-tryptamine compound according to claim 1 which is 3-(N-methylpyrrolidin-2S-ylmethyl)-5-[N-(t-butyloxycarbonyl)-3-aminopropyloxy]-1H-indole.

56. A 5-alkoxytryptamine compound according to claim 1 which is 3-(N-methylpyrrolidin-2R-ylmethyl)-5-(3-phthalimidopropyloxy)-1H-indole.

* * * * *